United States Patent
Arkles et al.

(10) Patent No.: US 10,513,637 B2
(45) Date of Patent: Dec. 24, 2019

(54) HIGH-SPEED MOISTURE-CURE HYBRID SILOXANE/SILSESQUIOXANE-URETHANE AND SILOXANE/SILSESQUIOXANE-EPOXY SYSTEMS WITH ADHESIVE PROPERTIES

(71) Applicant: Gelest Technologies, Inc., Morrisville, PA (US)

(72) Inventors: Barry C. Arkles, Pipersville, PA (US); Youlin Pan, Langhorne, PA (US)

(73) Assignee: Gelest Technologies, Inc., Morrisville, PA (US)

( * ) Notice: Subject to any disclaimer, the term of this patent is extended or adjusted under 35 U.S.C. 154(b) by 0 days.

(21) Appl. No.: 15/807,987

(22) Filed: Nov. 9, 2017

(65) Prior Publication Data

US 2018/0066165 A1    Mar. 8, 2018

Related U.S. Application Data

(62) Division of application No. 14/958,177, filed on Dec. 3, 2015, now Pat. No. 9,879,159.

(60) Provisional application No. 62/089,993, filed on Dec. 10, 2014.

(51) Int. Cl.

| | |
|---|---|
| *C07F 7/18* | (2006.01) |
| *C09J 11/06* | (2006.01) |
| *C08L 63/00* | (2006.01) |
| *C08G 18/71* | (2006.01) |
| *C08G 18/73* | (2006.01) |
| *C08G 18/28* | (2006.01) |
| *C08G 77/04* | (2006.01) |

(52) U.S. Cl.
CPC ............ *C09J 11/06* (2013.01); *C07F 7/1804* (2013.01); *C08G 18/289* (2013.01); *C08G 18/718* (2013.01); *C08G 18/73* (2013.01); *C08G 77/04* (2013.01); *C08L 63/00* (2013.01)

(58) Field of Classification Search
None
See application file for complete search history.

(56) References Cited

U.S. PATENT DOCUMENTS

| | | | |
|---|---|---|---|
| 3,993,708 | A | 11/1976 | Brinkmann et al. |
| 4,391,958 | A | 7/1983 | Minato et al. |
| 5,354,880 | A | 10/1994 | Pepe et al. |
| 5,777,144 | A | 7/1998 | Rubinsztajn et al. |
| 2004/0077892 | A1 | 4/2004 | Arkles et al. |
| 2007/0270563 | A1* | 11/2007 | Ziche ............... C07F 7/10 528/29 |
| 2010/0004414 | A1 | 1/2010 | Luo | |

FOREIGN PATENT DOCUMENTS

| | | |
|---|---|---|
| DE | 102004040314 A1 | 2/2006 |
| JP | 2000086904 A | 3/2000 |
| JP | 2011162497 A * | 8/2011 |
| JP | 2011162497 A | 8/2011 |
| KR | 20070033000 A | 3/2007 |
| WO | 9414820 A1 | 7/1994 |
| WO | 03091186 A2 | 11/2003 |

OTHER PUBLICATIONS

Google-MSDS—(N,N-dimethylaminopropyl)-aza-2-methyl-2-methoxysilacyclopentane.—2015 (Year: 2015).*
Google MSDS (Oct. 25, 2015) (Year: 2015).*
JP2011162497A (Aug. 25, 2011); (Year: 2011) Machine Translation.*
Int'l Preliminary Report on Patentability dated Jun. 22, 2017 in Int'l Application No. PCT/US2015/063717.
Office Action dated Jan. 25, 2017 in U.S. Appl. No. 14/958,177, by Arkles.
Office Action dated Aug. 28, 2017 in U.S. Appl. No. 14/958,177, by Arkles.
Office Action dated Jun. 14, 2018 in EP Application No. 15817644.6.
Speier et al. Syntheses of (3-Aminoalkyl)silicon Compounds. Journal of Organic Chemistry; 36(2) (1971).
Arkles, et al. Cyclica zasilanes—volatile coupling agents for nanotechnology. Silanes and Other Coupling Agents; vol. 3 p. 179-191 (2004).
Arkles, et al. Silicon Compounds: Silanes & Silicones: 3rd edition; Gelest; p. 142 (2013).
Int'l Search Report and Written Opinion dated Feb. 19, 2016 in Int'l Application No. PCT/US2015/063717.
Salikhov, T. et al., "Silylated Derivatives of Azasilacyclopentanes," Russian Journal of General Chemistry, vol. 84, No. 5, pp. 875-882 (2014).
Office Action dated Jan. 7, 2019 in EP Application No. 15817644.6.
Office Action dated Jul. 9, 2019 in KR Application No. 1020177018695.

* cited by examiner

*Primary Examiner* — Clinton A Brooks
*Assistant Examiner* — Kofi Adzamli
(74) *Attorney, Agent, or Firm* — Panitch Schwarze Belisario & Nadel LLP

(57) ABSTRACT

Materials containing the reaction products of a cyclic azasilane with water and a compound or polymer containing an isocyanate or epoxy functional group and methods for their synthesis are provided. Stable mixtures containing a cyclic azasilane and a compound or polymer containing an isocyanate or epoxy functional group according to invention are stored under anhydrous conditions. The invention also provides a novel class of materials, mono and bis(cycloaza) disiloxanes comprising one or two cyclic structures bridged by an Si—O—Si bond.

3 Claims, No Drawings

HIGH-SPEED MOISTURE-CURE HYBRID SILOXANE/SILSESQUIOXANE-URETHANE AND SILOXANE/SILSESQUIOXANE-EPOXY SYSTEMS WITH ADHESIVE PROPERTIES

CROSS-REFERENCE TO RELATED APPLICATIONS

This application is a divisional of co-pending U.S. patent application Ser. No. 14/958,177, filed Dec. 3, 2015, which claims priority from U.S. Provisional Patent Application No. 62/089,993, filed Dec. 10, 2014, the disclosures of which are herein incorporated by reference.

BACKGROUND OF THE INVENTION

Cyclic azasilanes are known to be moisture-gettering compounds which stop premature polymerization of silicone resins, as functionalizing end-cappers for silicone resins, and as volatile coupling agents. Moisture-activated cure epoxies have most commonly been prepared by utilizing imines, such as those disclosed in U.S. Pat. Nos. 4,391,958 and 3,993,708. In this art a Schiff base is formed by the reaction of a ketone or aldehyde with an amine, which precludes reaction with epoxy functionality. Typically, a ketimine functional material is mixed with an epoxy resin and stored under dry conditions. Upon introduction of water or moisture into the system, hydrolysis occurs, releasing a ketone or aldehyde; the protonated amine can then react with the epoxy group. Similarly, dimethylbutylidine blocked amino silanes have been utilized to form moisture-curable epoxy formulations with good adhesive properties as described by B. Arkles et al. (*Silicon Compounds: Silanes & Silicones*; 3rd edition; Gelest; p. 142 (2013)).

All of these systems react relatively slowly and liberate ketones or aldehydes as volatile byproducts which are not desirable, both in terms of film properties and worker exposure. Accordingly, improvements in speed of cure and reduction of byproducts are desirable.

BRIEF SUMMARY OF THE INVENTION

In a first embodiment, the invention is directed to a material comprising a reaction product of a cyclic azasilane with water and a compound or polymer comprising an isocyanate functional group.

In a second embodiment, the invention is directed to a material comprising a reaction product of a cyclic azasilane with water an a compound or polymer comprising an epoxy functional group.

In a third embodiment, the invention is directed to a stable mixture comprising a cyclic azasilane and a compound or polymer comprising an isocyanate or epoxy functional group, wherein the mixture is stored under anhydrous conditions.

A method for forming a hybrid siloxane/silsesquioxane-urethane or hybrid siloxane/silsesquioxane-epoxy material with adhesive properties involves first reacting a cyclic azasilane with a compound or polymer containing an isocyanate or epoxy functional group under low moisture conditions to form a reaction mixture and subsequently exposing the reaction mixture to moisture to form the desired hybrid material.

In further embodiments, the invention is directed to (N,N-dimethylaminopropyl)-aza-2-methyl-2-methoxysila-cyclopentane and (cycloaza)disiloxanes.

DETAILED DESCRIPTION OF THE INVENTION

This invention relates to one package mixed siloxane and silsesquioxane-urethane and siloxane and silsesquioxane-epoxy adhesive and film-forming compositions that are generated from mixtures of cyclic azasilanes with compounds or polymers containing isocyanate or epoxy functional groups. In other words, the invention relates to materials comprising the reaction products of cyclic azasilanes with water and compounds or polymers comprising isocyanate or epoxy functional groups. In both cases, additional fillers for control of rheological or mechanical properties may also be included in the mixture. As described in more detail below, the mechanism for the cure is based on the high speed moisture-induced ring opening of a cyclic azasilane which deprotects an amine functionality so that it can react directly with an isocyanate or epoxy functionality. In a second, slower, moisture-activated step, the cyclic azasilane both induces cross-linking and affords reactivity with substrates that possess hydroxyl groups.

According to the invention, cyclic azasilanes are mixed under low moisture conditions with compounds or polymers containing either isocyanate or epoxy functional groups. In one embodiment, a catalyst or accelerator, such as dibutyl-dilauryltin, dimethyltindineodecanote, or titanium diisopropoxide bis(pentanedionate) may be included in the reaction mixture. Under these conditions, there is no reactivity between the components. Thus, the invention is also directed to stable mixtures containing cyclic azasilanes and compounds or polymers comprising isocyanate or epoxy functional groups, which mixtures are stored under anhydrous conditions.

For example, as shown in the scheme below, isocyanatopropyltriethoxysilane and N-n-butyl-aza-2,2-dimethoxysila-cyclopentane are mixed together in 1:1 mole ratio with 1 mole percent dibutyldilautyltin under dry conditions. The mixture maintains a low viscosity liquid state. However, when the mixture is exposed to moisture, such as by spreading it as a thin film under normal atmospheric conditions (50-85% RH), an increase in viscosity is observed (typically in less than a minute). Within a few hours, depending on the specific composition, a solid film or bulk adhesive layer is formed. Similar results are observed when using isocyanatopropyltrimethoxysilane rather than isocyanatotriethoxysilane.

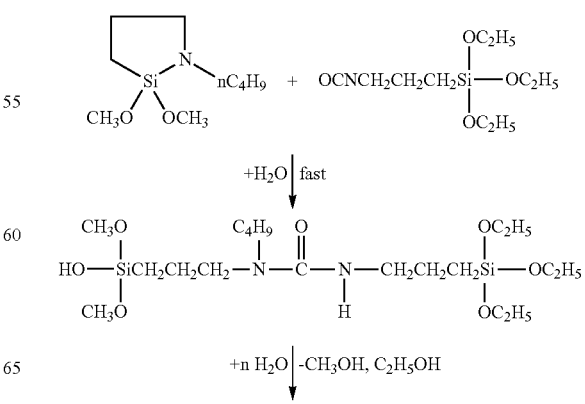

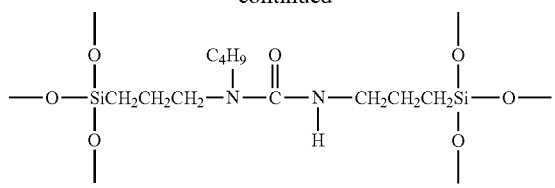

The observed adhesive characteristics are believed to be derived from the displacement of the alkoxy groups on the silicon by reaction with substrate hydroxyl groups. It should be noted that if stoichiometric quantities of water are added directly to the mixture, a sharp exotherm is observed. After this initial reaction, the mixture becomes a viscous liquid which can be spread as a film and will subsequently gel after exposure to atmospheric moisture.

Similarly, diisocyanates can react according to the following scheme. In preparing the initial blend of the isocyanate with the cyclic azasilane, it is critical to ensure that the isocyanate is dry (level of water below 100 ppm) to avoid premature gelation. Once water is added, the reaction proceeds rapidly.

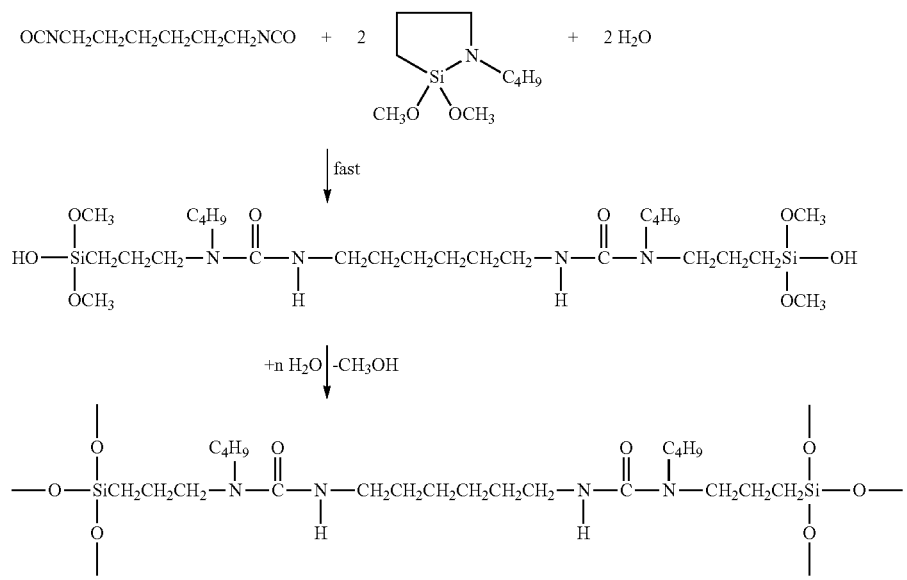

Difunctional epoxides may be mixed and reacted with N-n-butyl-aza-2,2-dimethoxysilacyclopentane (shown below) or (N,N-dimethylaminopropyl)-aza-2-methyl-2-methoxysilacyclopentane. Again, no reaction takes place under dry conditions. Once exposed to moisture under ambient conditions, thin films rapidly react to form tough adhesive layers. The (N,N-dimethylaminopropyl)-aza-2-methyl-2-methoxysilacyclopentane provides less brittle compositions that the N-n-butyl analog due to the fact it has fewer methoxy groups which, though hydrolysis, ultimately form siloxane cross-linking sites.

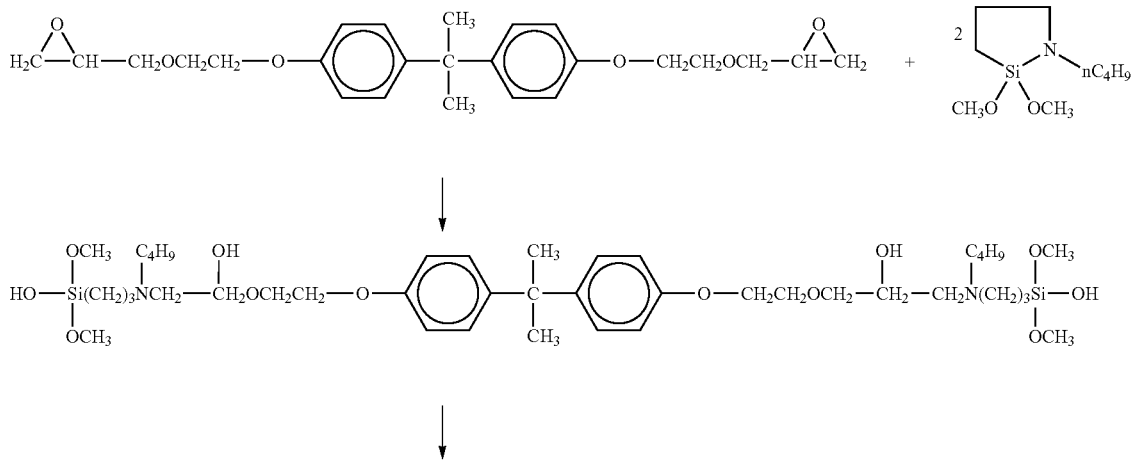

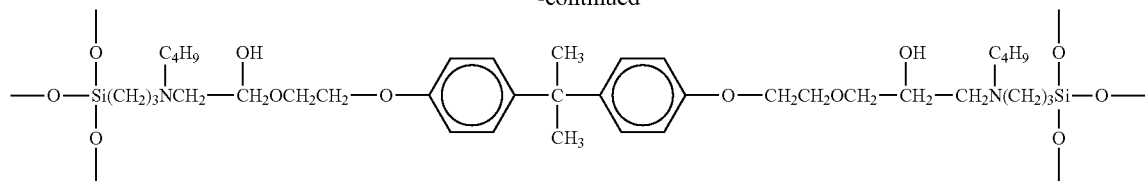

Bisphenol A derived epoxies, such as those shown below, can be reacted similarly, but require additional cyclic azasilane to react with hydroxyl groups.

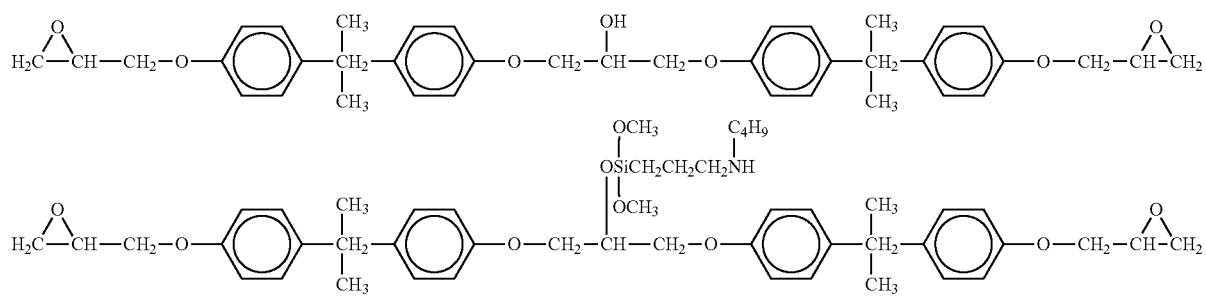

Similarly, N-n-butyl-aza-2,2-dimethoxysilacyclopentane can be mixed with 3-isocyanatopropyltriethoxysilane under dry conditions without reaction. However, upon exposure to moisture under ambient conditions of 5-85% RH, the mixture rapidly becomes viscous and then transforms to a translucent solid within a few hours.

It is also within the scope of the invention to form gels without formal crosslinking, as shown in the following exemplary reaction.

-continued

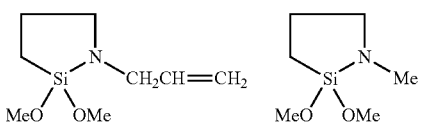

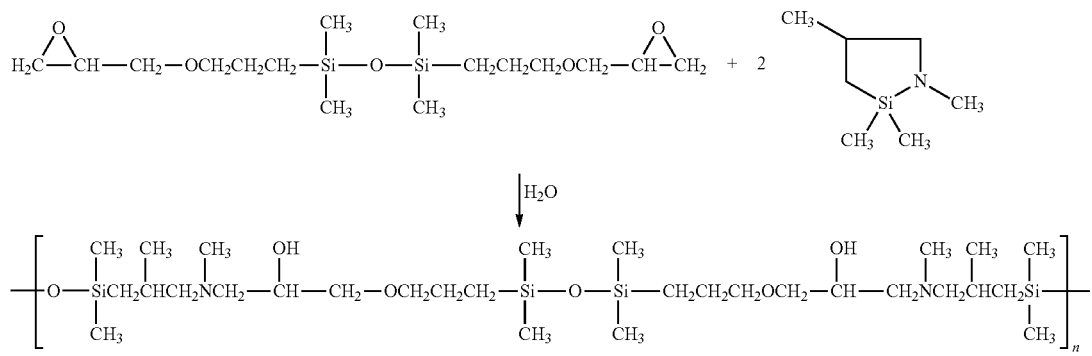

While a wide variety of epoxy and isocyanate compounds and polymers may be used, it is preferred if the compound or polymer contains at least two reactive groups.

A variety of cyclic azasilanes may be used in the invention, including without limitation the following compounds:

-continued

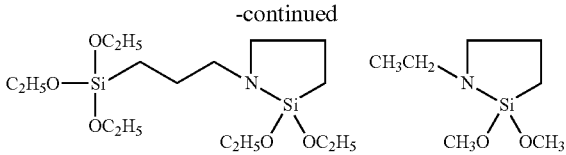

It is also within the scope of the invention to utilize the novel cyclic azasilane, (N,N-dimethylaminopropyl)-aza-2-methyl-2-methoxysilacyclopentane, which is also encompassed by the invention, and which has the following structure:

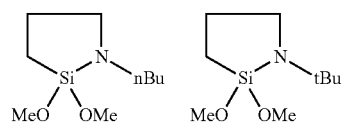

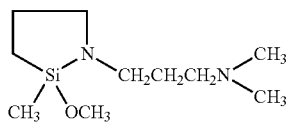

The synthesis of analogous compounds are described in U.S. Patent Application Publication No. 2004/0077892 of Applicants, which is herein incorporated by reference. Briefly, 3-(N,N-dimethylaminopropylamino)propylmethyldmethoxysilane is heated with 2 mole % ammonium sulfate. Methanol is removed slowly under low vacuum conditions, giving an equilibrium mixture of cyclic and oligomeric species. When the formation of methanol approaches stoichiometry, vacuum is increased and the cyclic azasilane is distilled from the equilibrating mixture.

It is also within the scope of the invention to utilize bis(cycloaza)disiloxanes, such as bis(n-butyl-1-methoxycycloaza-1-silacyclopentyl)ether:

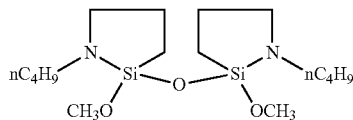

Mono and bis(cycloaza)silanes are a novel class of compound which are also encompassed by the present invention. These compounds comprise one or two cyclic structures bridged by an Si—O—Si bond. Other specific examples of these compounds which are included in the invention include N-alkylaminoalkylcyclodisiloxanes, in which there is one cyclic structure bridged to another silicon atom by an Si—O—Si bond, and N-butyl-1-methoxy-1-(n-butylaminopropyldimethoxysiloxy)cycloazasilane. That is, a disiloxane structure in which only one of the cyclic rings is formed also has utility as a curing agent. For bis(n-butyl-1-methoxycycloaza)disiloxane, the single cyclic ring structure is n-butyl-1-methoxy-1-(n-butylaminopropyldimethoxylsiloxy)cycloazasilane.

Since bis(cycloaza)silanes do not rely on the relatively slow hydrolysis of alkoxy groups bound to silicon, compared to the high-speed hydrolysis of the Si—N bond, the rate of cure is accelerated. In a sense, the S—O—Si bond is formed in advance of the primary ring-opening reaction rather than after it.

In addition to the materials, stable mixtures, and compounds described previously, the invention also relates to methods for forming the materials described above. Specifically, a method for forming a hybrid siloxane/silsesquioxane-urethane or hybrid siloxane/silsesquioxane-epoxy material with adhesive properties involves first reacting a cyclic azasilane with a compound or polymer containing an isocyanate or epoxy functional group under low moisture conditions, to form a reaction mixture. While any water molecules will consume azasilane and initiate the product formation, it may be understood that the exposure of water cannot be so great so as to increase the viscosity of the reaction mixture such that it is not pourable. Optionally, the reaction mixture further comprises a catalyst or accelerator, such as dibutyldilauryltin, dimethyltindineodecanote, or titanium diisopropoxide bis(pentanedionate). The reaction mixture may be stored under anhydrous conditions for six months or even longer. Subsequently, the reaction mixture is exposed to moisture (preferably 50-85% relative humidity) to form the desired hybrid material.

The invention may be understood in conjunction with the following, non-limiting examples.

EXAMPLE 1: REACTION OF N—N-BUTYL-AZA-2,2-DIMETHOXY-SILYLCYCLOPENTANE WITH 3-ISOCYANOTOPROPYLTRIMETHOXYSILANE

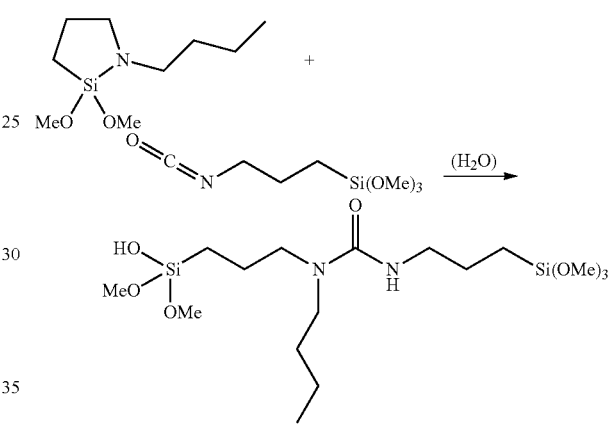

A 25 ml three neck flask equipped with magnetic stirrer, pot thermometer, rubber septum, and an adapter connected to a $N_2$ bubbler was charged with 1.0 g (5 mmol) of N-n-butyl-aza-2,2-dimethoxysilylcyclopentane. 1.0 g (5 mmol) of 3-isocyanotopropyltrimethoxysilane was added in about 5 min. No exotherm was observed and the mixture remained liquid. After being stirred at room temperature for 15 min, two drops of water were added, the pot temperature rose 6° C., and a very viscous liquid formed. One drop of the mixture was placed on a glass slide and a pale yellow film formed in about two hours.

EXAMPLE 2: REACTION OF N—N-BUTYL-AZA-2,2-DIMETHOXY-SILACYCLOPENTANE WITH 1,3 BIS(GLYCIDOXYPROPYL)TETRAMETHYLDISILOXANE

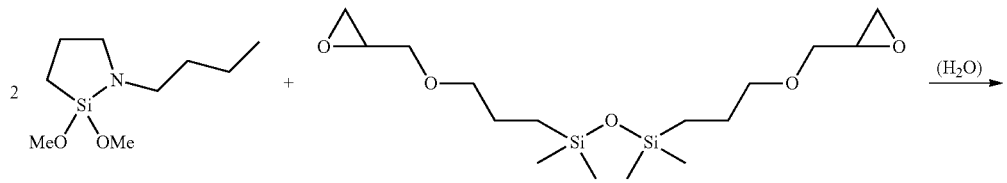

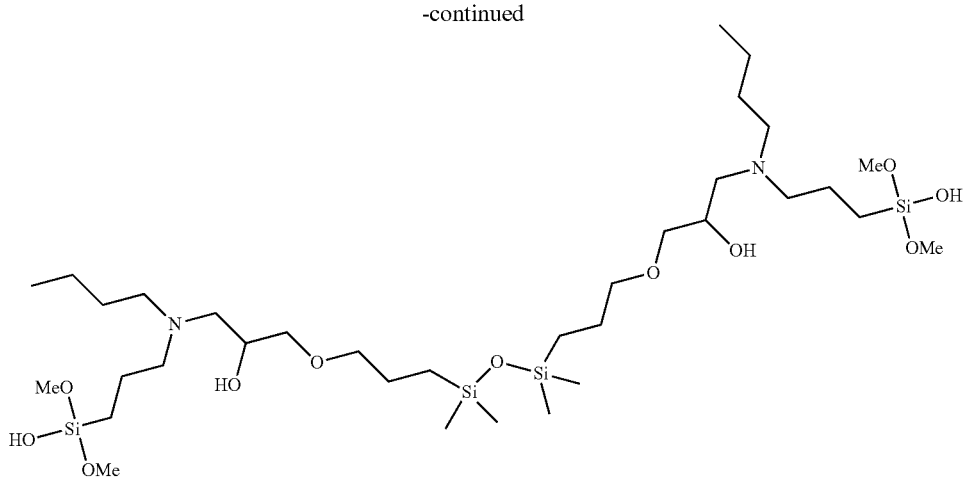

A 250 ml three neck flask equipped with magnetic stirrer, pot thermometer, rubber septum, and an adapter connected to a $N_2$ bubbler was charged with 40.7 g (0.2 mol) of N-n-butyl-aza-2,2-dimethoxysilylcyclopentane. 36.3 g (0.1 mol) of 1,3-bis(glycidoxypropyl)tetramethyldisiloxane were added over 15 min. No exotherm was observed and the mixture remained liquid. After being stirred at room temperature for 2 hours, 3.6 g (0.2 mol) of water were added, the pot temperature rose from 20 to 31° C. over 10 min, and a very viscous liquid formed. After being stirred at room temperature for 3 hours, the pot temperature rose another 6° C. over 10 min and a gel-like material formed.

EXAMPLE 3: REACTION OF N—N-BUTYL-AZA-2,2-DIMETHOXY-SILACYCLOPENTANE WITH 1,6-DIISOCYANATOHEXANE

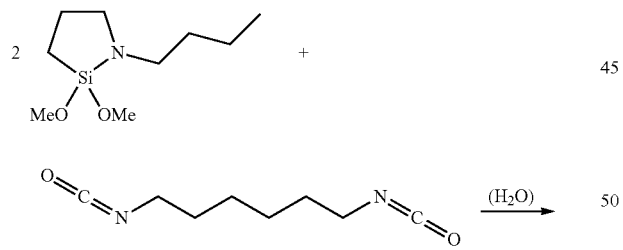

A 25 ml three neck flask equipped with magnetic stirrer, pot thermometer, rubber septum, and an adapter connected to a $N_2$ bubbler was charged with 1.0 g (5 mmol) of N-n-butyl-aza-2,2-dimethoxysilylcyclopentane. 0.4 g (2.5 mmol) of 1,6-diisocyanatohexane was added. No exotherm was observed and the mixture remained a liquid. After being stirred at room temperature for 15 min, two drops of water were added, the pot temperature rose 7° C., and a very viscous liquid formed. One drop of the mixture was placed on a glass slide and pale yellow solids formed in about two hours.

EXAMPLE 4: REACTION OF N—N-BUTYL-AZA-2,2-DIMETHOXY-SILACYCLOPENTANE WITH BISPHENOL A

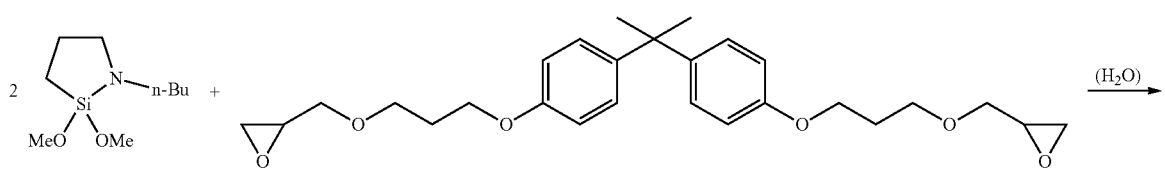

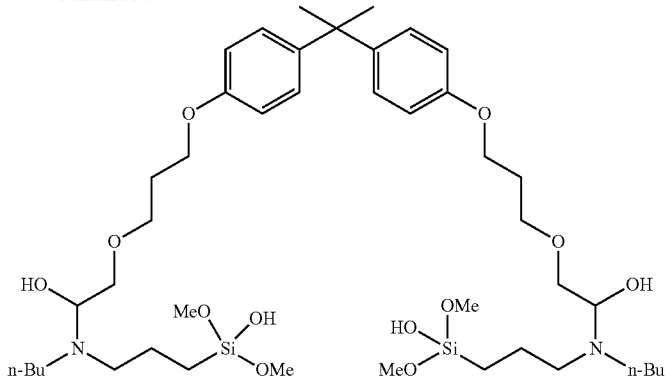

A 250 ml three neck flask equipped with magnetic stirrer, pot thermometer, rubber septum, and an adapter connected to a N₂ bubbler was charged with 20.3 g (0.1 mol) of N-n-butyl-aza-silacyclopentane. 22.8 g (0.05 mol) of bisphenol-A propoxylate diglycidyl ether were added over 15 min. A very mild exotherm was observed (about 3° C.) and the mixture remained liquid. After being stirred at room temperature for four hours, 0.8 g of water was added. The pot temperature rose from 20 to 27° C. over 10 min and a very viscous liquid formed. After being stirred at room temperature for 1 hour, 1.0 g of water was added, the pot temperature rose from 20 to 25° C. over 10 min, and a solid mass formed.

EXAMPLE 5: FORMATION OF N-BUTYL-AZA-2,2-DIMETHOXY-SILACYCLOPENTANE

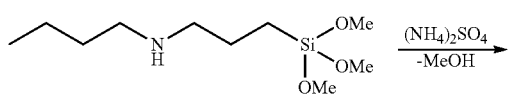

A 2000 ml three neck flask equipped with magnetic stirrer, pot thermometer, and four foot long packing column with a distillation head was charged with 588.5 g (2.5 mol) of n-butylamino-propyltrimethoxysilane and 2.5 g of (NH₄)₂SO₄. The pot mixture was heated at 160 to 180° C. with ~50 mmHg over 20 to 40 hours. Methanol was removed from the pot at its formation and crude product mixture was collected in a receiver. Redistillation of the crude afforded the pure title compound: 339 g (53%). FTIR and GC-MS confirmed the structure of products. MS: m/z (%): 203 (M+, 7), 160(M+—C3H7, 100).

EXAMPLE 6: FORMATION OF N-BUTYL-1-METHOXY-1-(N-BUTYLAMINOPROPYLDIMETHOXYSILOXY)CYCLOAZASILANE AND BIS (N-BUTYL-1-METHOXYCYCLOAZA-1-SILACYCLOPENTYL)ETHER

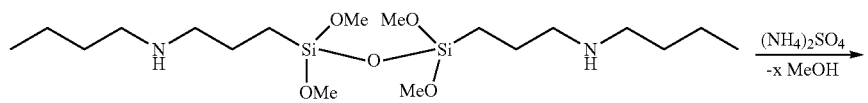

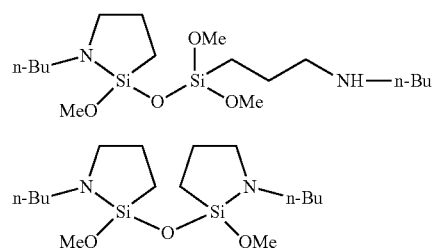

A 2000 ml three neck flask equipped with magnetic stirrer, pot thermometer, and a one foot long packed column mounted with a distillation head was charged with 637.1 g (1.5 mol) of 1,3-di(n-butylamino)propyl-1,1,3,3-tetramethoxydisiloxane and 3.2 g of (NH4)2SO4. The pot mixture was heated at 160 to 180° C. at ~2 to 5 mmHg over 20 to 40 hours. Methanol was removed from the pot at its formation. The resulted pot crude was then distilled with 0.3 mmHg at a pot temperature below 180° C. to afford 179 g (37%) of a mixture of monocyclic and bicyclic compounds: FTIR and GC-MS confirmed the structure of products. MS of the monocyclic: m/z (%), 392 (M+, 1%), 360(M+—MeOH), 317(M+—MeOH—C3H7, 100%). MS of the bicyclic: m/z (%), 360(M+, 5%), 317(M+—C3H7, 100%).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A stable mixture comprising a monomeric cyclic azasilane and a compound or polymer comprising an isocyanate or epoxy functional group, wherein the mixture is stored under anhydrous conditions, and wherein no reaction occurs between the monomeric cyclic azasilane and the compound or polymer.

2. The mixture according to claim 1, wherein the cyclic azasilane is selected from azasilanes having the following structures:

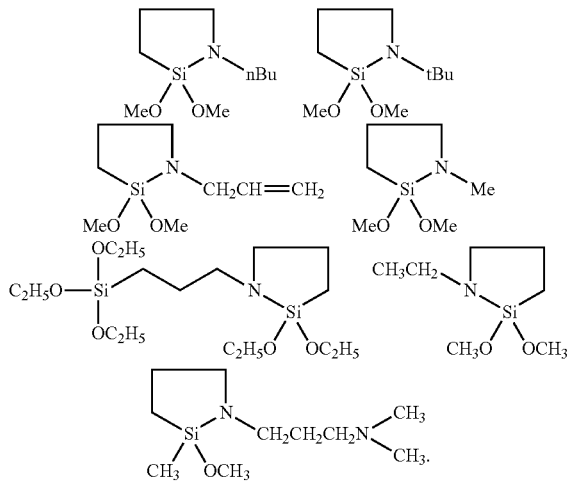

3. (N,N-dimethylaminopropyl)-aza-2-methyl-2-methoxysilacyclopentane.

* * * * *